United States Patent [19]

Mori et al.

[11] 4,038,416
[45] July 26, 1977

[54] PHARMACEUTICAL COMPOSITION AND METHOD OF THE USE THEREOF

[75] Inventors: Takashi Mori, Tama; Sakae Takaku, Ageo; Nobuhiro Oi, Hoya; Minoru Shindo, Higashikurume; Takeaki Hirano, Fujimi; Shigeyuki Kataoka, Saitama; Kouji Furuno, Kokubunji, all of Japan

[73] Assignee: Chugai Seiyaku Kabushiki Kaisha, Tokyo, Japan

[21] Appl. No.: 612,500

[22] Filed: Sept. 11, 1975

[51] Int. Cl.² .......................................... A61K 31/165
[52] U.S. Cl. ................................ 424/324; 260/558 P
[58] Field of Search ..................... 424/324; 260/558 P

[56] References Cited

U.S. PATENT DOCUMENTS 3,937,729  2/1976  Teach ................................. 260/557

Primary Examiner—Frederick E. Waddell
Attorney, Agent, or Firm—Browdy and Neimark

[57] ABSTRACT

A pharmaceutical composition for prevention and treatment of gastritis and peptic ulcer of mammals including human beings which contains a bis(benzamido)-benzene derivative represented by the formula

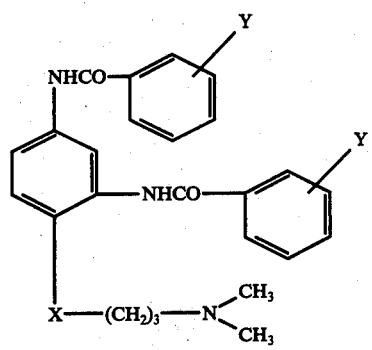

wherein X and Y are as defined hereinbelow or an acid addition salt thereof as an active ingredient, and a method of the use thereof are disclosed.

17 Claims, 4 Drawing Figures

CHANGE OF BODY WEIGHT OF RATS ADMINISTERED WITH 1-(3'-DIMETHYLAMINOPROPOXY)-2,4-BIS(3''-METHYLBENZAMIDO)-BENZENE

CHANGE OF BODY WEIGHT OF PATS ADMINISTERED WITH
1-[N-(3'-DIMETHYLAMINOPROPYL)-CARBAMOYL]
-2,4-BIS(2"-METHYLBENZAMIDO)-BENZENE

CHANGE OF BODY WEIGHT OF RATS ADMINISTERED WITH
1-[N-(3'-DIMETHYLAMINOPROPYL)-CARBAMOYL]-2,4-BIS(3"-METHYLBENZAMIDO)-BENZENE

PHARMACEUTICAL COMPOSITION AND METHOD OF THE USE THEREOF

BACKGROUND OF THE INVENTION

1. Field of the Invention

This invention relates to a pharmaceutical composition for prevention and treatment of gastritis and peptic ulcer of mammals including human beings and a method of the use thereof, and particularly, it relates to a pharmaceutical composition for prevention and treatment of gastritis and peptic ulcer which contains a bis(benzamido)-benzene derivative as an effective ingredient and a method of the use thereof.

2. Description of the Prior Art

It is understood that peptic ulcer and gastritis are induced by various causes, such as anxiety, smoking, intake of an alcoholic drink, excessive intake of stimulative foods, and therefore, in order to treat or prevent the peptic ulcer a specific method or a specific pharmaceutical composition should be selected depending on the cause of the ulcer.

In general, remedies may be classed based on the type of activity as follows.

a. antidigestive agents (antacids and antipepsins)
b. gastric antisecretory agents (anticholinergics, local anesthetics and gastro-intestinal hormones)
c. protective agents (antipepsins, astringents and demulcents)
d. tissue regeneration accelerators (mucus formation accelerators)

For this purpose, various type of remedy other than those listed above such as sedatives, tranquilizer and the like are often used.

SUMMARY OF THE INVENTION

The inventors of this invention have studied the pharmacological activities of bis(benzamido)-benzene derivatives and have finally found an excellent and new type of anti-ulcer compound. They have continued their study to produce a pharmaceutical composition containing a derivative and a method of the use thereof.

DESCRIPTION OF THE PREFERRED EMBODIMENTS

Figure 1:
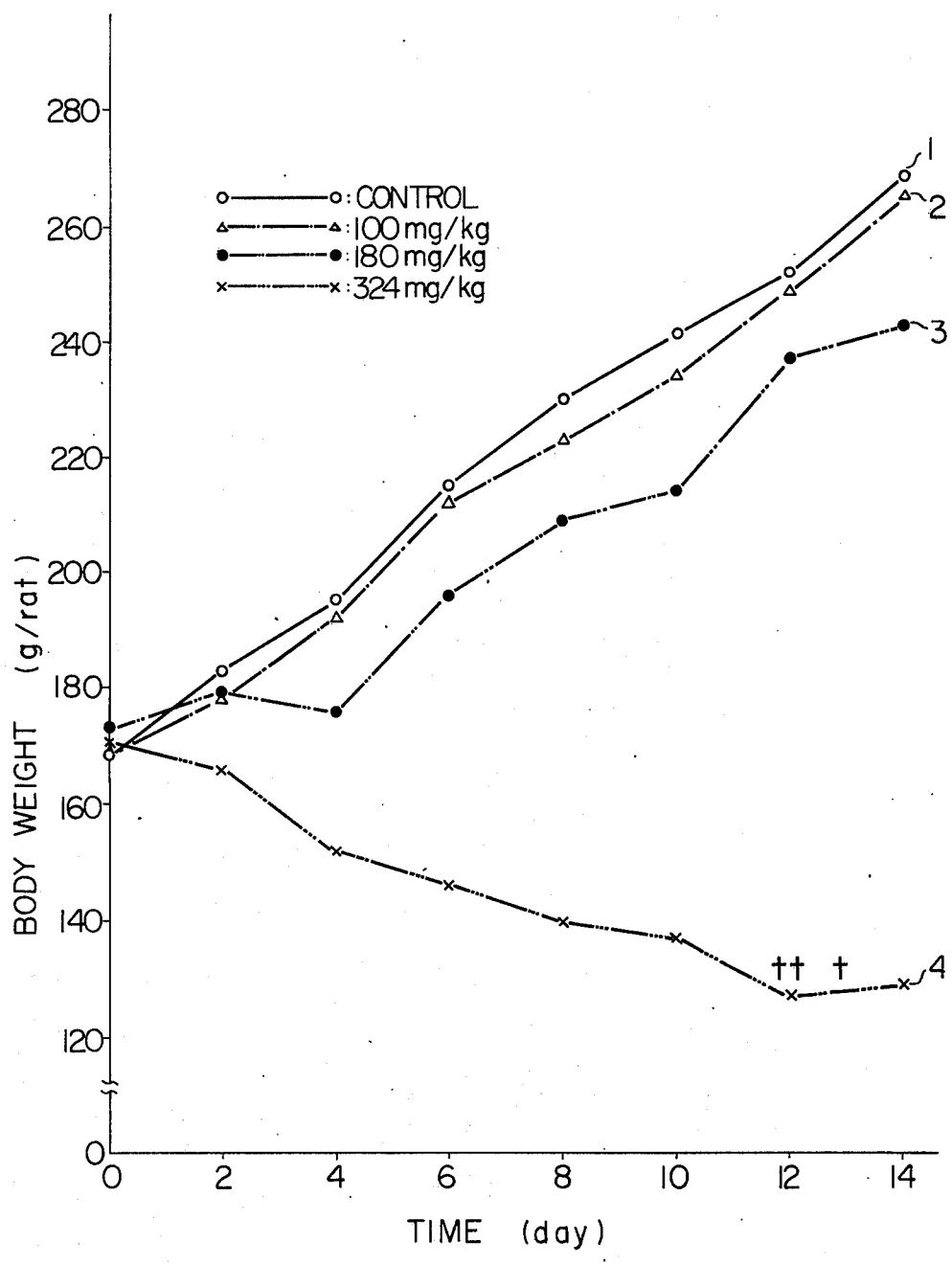
FIGS. 1, 2, 3 and 4 show the change in weight of rats which wereadministered a test compound once a day were administered for 14 days. The compounds used for FIGS. 1, 2, 3 and 4 are 1-(3'-dimethylaminopropoxy)-2,4-bis(2''-methylbenzamido)-benzene, 1-(3'-dimethylaminopropyoxy)-2,4-bis(3''-methylbenzamido)-benzene, 1-[N-(3'-dimethylaminopropyl)-carbamoyl]-2,4-bis(2''-methylbenzamido)-benzene and 1-[N-(3'-dimethylaminopropyl)-carbamoyl] 2,4-bis(3''-methylbenzamido)-benzene, respectively. In the Figures, curve 1 corresponds to the control group and curves 2, 3 and 4 correspond to the groups of rats administered with the test compound in a dose of 100, 180 and 324 mg/kg.body weight per day, respectively. The symbol "+" means the number of rats that died on the indicated day.

One embodiment of this invention is a pharmaceutical composition for prevention and treatment of gastritis and peptic ulcer of mammals including human beings which comprises a bis(benzamido)-benzene derivative represented by the formula

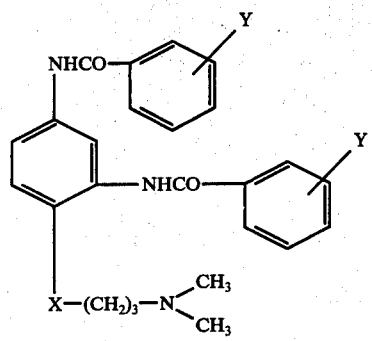

wherein X is oxygen or -CONH- and Y is methyl attached to o- or m-position of the benzene nucleus or an acid addition salt thereof in an amount sufficient to realize prevention and treatment of peptic ulcer and gastritis and a pharmaceutically acceptable carrier.

Among the compounds represented by formula (I), 1-(3'-dimethylaminopropoxy)-2,4-bis(2''-methylbenzamido)benzene, 1-3'-dimethylaminopropoxy)-2,4-bis(3''-methylbenzamido)-benzene, 1-[N-(3'-dimethylaminopropyl)carbamoyl]-2,4-bis(2''-methylbenzamido)-benzene and 1-[N-(3'-dimethylaminopropyl)-carbamoyl]-2,4-bis(3''-methylbenzamido)-benzene are preferable. All these particular compounds are novel.

The compound represented by formula (I) wherein X is oxygen is prepared, for example, by reacting 1-(3'-dimethylaminopropoxy)-2,4-diaminobenzene with a compound represented by the formula

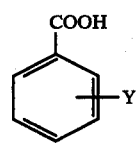

wherein Y is as defined for formula (I) above or a reactive derivative thereof on its carboxyl radical.

The compound represented by formula (I) wherein X is —CONH— is prepared, for example, by reacting 2,4-diaminobenzoic acid with a compound represented by formula (II) or the reactive derivative thereof and further reacting the resulting intermediate with 3-dimethylamino-1-propylamine.

Since the bis(benzamido)-benzene derivative according to this invention is hardly soluble in water, it is used as a suspension in an aqueous solution of carboxymethyl cellulose, gum arabic or the like or used as a solution of its inorganic or organic acid addition salt in a sucrose aqueous solution. The derivative may be formulated by mixing it with a conventional, pharmaceutically acceptable carrier such as lactose, starch, crystalline cellulose, kaolin, calcium carbonate, talc or the like to form tablets, granules or powder. The granules and powder may be charged into capsules. An inorganic or organic acid addition salt, for example, a hydrochloride, may be dissolved, for example, in a distilled water containing benzyl alcohol to prepare parenteral injections.

The amount of the bis(benzamido)-benzene in the formulated composition may vary depending on the form of the composition and the animal to be administered. However, since desired activities can be obtained by the oral administration of the derivative in an amount more than 0.01 mg/kg.body weight per day once a day for several days, the derivative may be present in the composition in an amount sufficient to realize the administration in a dose level of usually 0.01–100, preferably 0.05–20 mg/kg.body weight per day.

On the other hand, for parenteral injection the derivative is present in an amount sufficient to realize the administration in a dose level of usually 0.002 – 10, preferably 0.01–2 mg/kg.body weight per day.

The compositions may contain a conventional anti-ulcer agent such as alumina gel, sucrose polysulfate aluminum powder of licorice, L-glutamine, sodium bicarbonate, aluminium silicate, magnesium silicate and the like.

Another embodiment of this invention is a method for prevention and treatment of gastritis and peptic ulcer of mammals including human beings by the administration of the pharmaceutical composition as disclosed above.

In order to realize the prevention and treatment of peptic ulcer and gastritis by the use of the pharmaceutical composition prepared in a manner disclosed in the first embodiment, a mammal in which peptic ulcer or gastritis is to be prevented or treated is administered orally or by subcutaneous, intramuscular or intravenous injection with the composition one or more times per day. In particular, for human beings, administration three times per day, i.e. after every meal is preferred. For mammals other than human beings, the pharmaceutical composition may be used as it is or mixed with foods. Although the amount to be used varies depending on the kind of animal and the type of composition, it ranges usually from 0.01–100 mg/kg, preferably 0.05–20 mg/kg. body weight per day for the oral administration, and usually 0.002–10, preferably 0.01–2 mg/kg. body weight per day for the injection. In case human beings are orally administered with a tablet containing 5–50 mg of the active ingredient after every meal, satisfactory results will be obtained, though the study has not been completed.

In accordance with this invention, peptic ulcer and gastritis of various kinds of mammals, for example, human being, monkey, bovine, horse, dog, cat, pig and the like can be prevented or treated by the administration of the pharmaceutical composition of this invention.

This invention will be further illustrated by the following Examples and Preparation Examples. However, they are not to be construed as limiting the scope of this invention.

Preparation of Active Ingredients 1. 2,4-Diaminobenzoic acid (15.2g) was dissolved in pyridine (300 ml) followed by cooling the solution with ice-water, and then 2-methylbenzoylchloride (62 g) was added dropwise to the solution over 10 minutes while stirring. The mixture was heated on steam bath for 2 hours and allowed to stand for cooling. Water (300 ml) was added to the mixture and the resulting crystals were recovered by filtration. The crystals were washed with toluene, dried and recrystallized from ethyl acetate to obtain pure crystals. After drying them, the crystals (18.5 g) were dissolved in tetrahydrofuran (100 ml), and 3-dimethylamino-1-propylamine (6.7 g) was added to the solution followed by heating it at reflux for 3 hours. After allowing it to cool, water (300 ml) was added to it to precipitate crystals. The crystals were recovered by filtration, washed with water, dried, purified through a silica gel column chromatography and re-crystallized from ethyl acetate containing water to obtain 1-[N-(3'-dimethylaminopropyl)-carbamoyl]-2,4-bis(2"-methylbenzamido)-benzene (19 g) having a melting point between 164-165° C.

Elemental Analysis:
Calcd. for $C_{28}H_{32}O_3N_4$: C, 71.2; H, 6.8; N, 11.9 (%);
Found : C, 71.1; H, 6.9; N, 11.8 (%).

In a procedure similar to that described in the above, 1-[N-(3'-dimethylaminopropyl)-carbamoyl]-2,4-bis(3"-methylbenzamido)-benzene having a melting point between 172°–173° C was prepared.

Elemental Analysis:
Calcd. for $C_{28}H_{32}O_3N_4$ : C, 71.2; H, 6.8; N, 11.9 (%);
Found : C, 71.0; H, 6.9; N, 11.7 (%).

2. To a mixture of potassium carbonate (25 g), water (50 ml) and tetrahydrofuran (130 ml) was added 1-(3'-dimethylaminopropoxy)-2,4-diaminobenzene trihydrochloride (9.6 g) while stirring under cooling and immediately after the addition 3-methylbenzoylchloride (15 g) was added to the resulting mixture at a time. Then the cooling was terminated and the stirring was continued at room temperature for 1 hour and then at a temperature of from 40° to 50° C for 2 hours. After the completion of the reaction, the reaction mixture was extracted with benzene and basic substances in the benzene layer were transferred to an aqueous layer with the use of a diluted hydrochloric acid. In case the hydrochloride salt did not completely dissolve in water, a small amount of methanol was used to completely dissolve it. After washing the water layer with diethyl ether, the pH of the layer was adjusted to 9-10 with potassium carbonate and extracted with benzene. The benzene layer was washed with water, dried and condensed. The residue was purified with silica gel column chromatography and recrystallized from benzene-diethyl ether to obtain 9.1 g of 1-(3'-dimethylaminopropoxy)-2,4-bis)3"-methylbenzamido-benzene having a melting point between 120-121° C.

Elemental Analysis:
Calcd. for $C_{27}H_{31}N_3O_3$: C, 72.8; H, 7.0; N, 9.4 (%);
Found : C, 72.9; H, 7.2; N, 9.3 (%).

In the manner similar to that described above, 1-(3'-dimethylaminopropoxy)-2,4-bis(2"-methylbenzamido-benzene having a melting point between 136°-137° C was prepared.

Elemental Analysis:
Calcd. for $C_{27}H_{31}N_3O_3$: C, 72.8; H, 7.0; N, 9.4 (%);
Found : C, 72.9; H, 7.1; N, 9.5 (%).

EXAMPLE 1

Protective Action on pylorus ligature ulcer formation

The pylorus of Sprague-Dawley strain male rats weighing 150–200 g that had abstained from food, but not water for 48 hours was ligatured under ether anethsia. Each rat was allowed to stand individually in a cage for 16 hours without food and water. At the end of this term, the rats were sacrificed by an overdose of diethyl ether. The stomach was taken out of each animal and the gastric mucosa was observed by the use of a dissecting microscope.

Ulcers observed in the gastric mucosa were evaluated on a scale of from 0 to 5 defined as follows.

0: No lesion was observed.
1: Hemorrhage and/or erosion were observed.
2: One to five small ulcers less than 3 mm in diameter were observed.

3: Six or more small ulcers and/or a large ulcer more than 3 mm in diameter were observed.
4: Two or more large ulcers were observed.
5: At least one perforating ulcer was observed.

A test compound was administered as an aqueous solution in an equivalent molar of hydrochloric acid in the duodenum immediately after the pylorus ligature.

The results are shown in Table I.

limbs with a strand. The fixed rats were submerged in water bath to the depth of ensiform process with their hind legs dipped first. Sixteen hours after the submerge, the rats were brought out from the bath and their stomachs were taken out. After light fixation with a 1% formalin aqueous solution, the stomach of each animal was cut open along their greater curvature and gastric mucosa was observed through a dissecting microscope.

Table I

| Test Compound | Dose (mg/kg) | Number of Animals | Death Rate | Percent Perforating Ulcers | Ulcer Index (mean value ± standard deviation) | Percent Inhibition |
|---|---|---|---|---|---|---|
| Control | — | 9 | 47 | 56 | 4.0 ± 1.3 | — |
| 1-(3'-dimethylaminopropoxy)-2,4-bis(2''-methylbenzamido)-benzene | 50 | 5 | 20 | 20 | 3.2 ± 1.3 | 20 |
|  | 100 | 5 | 0 | 0 | 2.6 ± 0.5* | 35 |
|  | 200 | 5 | 0 | 0 | 0*** | 100 |
| 1-(3'-dimethylaminopropoxy)-2,4-bis(3''-methylbenzamido)-benzene | 50 | 6 | 33 | 50 | 4.0 ± 1.1 | 0 |
|  | 100 | 6 | 0 | 0 | 2.0 ± 1.4* | 50 |
|  | 200 | 6 | 0 | 0 | 1.0 ± 1.1*** | 75 |
| 1-[N-(3'-dimethylaminopropyl)-carbamoyl]-2,4-bis(2''-methylbenzamido)-benzene | 200 | 7 | 0 | 0 | 1.4 ± 1.4** | 65 |
| 1-[N-(3'-dimethylaminopropyl)-carbamoyl]-2,4-bis(3''-methylbenzamido)-benzene | 200 | 6 | 0 | 0 | 2.5 ± 1.4* | 38 |

*P<0.05
**P<0.01
***P<0.001

As is clear from Table I, the administration of 1-(3'-dimethylaminopropoxy)-2,4-bis(2''-methylbenzamido)-benzene or 1-(3'-dimethylaminopropoxy)-2,4-bis(3''-methylbenzamido)-benzene in a dose of 100 mg/kg or 200 mg/kg, or the administration of 1-[N-(3'-dimethylaminopropyl)-carbamoyl]-2,4-bis(2''-methylbenzamido)-benzene or 1-[N-(3'-dimethylaminopropyl)carbamoyl]-2,4-bis(3''-methylbenzamido)-benzene in a dose of 200 mg/kg not only completely inhibited the death of rats and the formation of perforating ulcers, but also prevented the formation of gastric ulcers on a statistically significant level.

The ulcer was evaluated on an ulcer index calculated from the following equation:

Ulcer Index = a + b/10 wherein $a$ is the number of big ulcers more than 3 mm in diameter and $b$ is the number of small ulcers up to 3 mm in diameter.

A test compound was orally administered as a suspension in a 1% gum arabic aqueous solution, 10 minutes before exposure to stress.

The results are shown in Table II below.

Table II

| Test Compound | Dose (mg/kg) | Number of Animals | Number of Ulcers/Stomach up to 3 mm | 3 mm or larger | Ulcer Index (mean value ± standard deviation) | Percent Inhibition |
|---|---|---|---|---|---|---|
| Control | — | 10 | 45.6 | 1.3 | 6.1 ± 2.3 | — |
| 1-(3'-dimethylaminopropoxy)-2,4-bis(2''-methylbenzamido)-benzene | 30 | 5 | 23.4 | 0.6 | 2.8 ± 0.8** | 54 |
|  | 45 | 6 | 16.8 | 0.2 | 2.0 ± 0.6*** | 67 |
|  | 67 | 6 | 8.8 | 0.2 | 1.0 ± 0.9*** | 84 |
|  | 100 | 5 | 3.8 | 0 | 0.4 ± 0.5*** | 93 |
| 1-(3'-dimethylaminopropoxy)-2,4-bis(3''-methylbenzamido)-benzene | 30 | 5 | 21.4 | 0.5 | 2.6 ± 2.1* | 57 |
|  | 45 | 6 | 8.7 | 1.0 | 2.0 ± 1.7** | 67 |
|  | 67 | 6 | 7.3 | 0.8 | 1.5 ± 2.7** | 75 |
|  | 100 | 5 | 10.6 | 0.8 | 2.0 ± 2.1** | 67 |
| 1-[N-(3'-dimethylaminopropyl)-carbamoyl]-2,4-bis(2''-methylbenzamido)-benzene | 100 | 5 | 23.4 | 0.8 | 3.0 ± 1.0* | 51 |
| 1-[N-(3'-dimethylaminopropyl)-carbamoyl]-2,4-bis(3''-methylbenzamido)-benzene | 100 | 5 | 17.6 | 0.6 | 2.4 ± 2.1** | 61 |

*P<0.05
**P<0.01
***P<0.001

EXAMPLE 2

Action on stress-induced ulcer formation

Sprague-Dawley strain male rats weighing 200–250 g were deprived of food for 24 hours, and then laid down on their backs on a screen and fixed by fastening their As is clear from Table II, the administration of 1-(3'-dimethylaminopropoxy)-2,4-bis(2''-methylbenzamido)-benzene or 1-(3'-dimethylaminopropoxy)-2,4-bis(3''-methylbenzamido)-benzene shows a 50–60% inhibition of the formation of ulcer even in a dose of 30 mg/kg.body weight and this inhibiting action increases as the dose level heightens. On the other hand, 1-[N-(3'-dimethylaminopropyl)-carbamoyl]-2,4-bis(2''-methylbenzamido)-benzene and 1-[N-(3'-dimethylaminopropyl)-carbamoyl[-2,4-bis(3''-methylbenzamido)-benzene realizes a 50–60% inhibition by the administration in a dose of 100 mg/kg.body weight.

EXAMPLE 3

Action on the healing of acetic acid ulcers

Sprague-Dawley strain male rats (8 weeks old) were etherized and their abdominal parts were cut open. A 20% acetic acid aqueous solution (0.05 ml) was injected into subserosal layer in the glandular part of stomach of each rat and the incisions were sutured.

From the fourth day after the operation, each rat was orally administered with 1-(3'-dimethylaminopropoxy)-2,4-bis(3''-methylbenzamido)-benzene in a dose of 10 mg/kg or 40 mg/kg.body weight as an aqueous solution in an equivalent molar of hydrochloric acid once a day for 15 days. On the day after the last administration, the rats were sacrificed by an overdose of diethyl ether and the stomach of each of the rats was taken out. After light fixation of the stomach with a 1% formalin solution, it was cut open along the greater curvature and the gastric mucosa was observed through a dissecting microscope. The ulcer was evaluated as the product ($mm^2$) of the major axis and the minor axis of the ulcer.

The results are shown in Table III.

Table III

| | Action on the healing of acetic acid ulcer | | | |
|---|---|---|---|---|
| Test Compound | Dose (mg/kg) | Number of animals | Ulcer Index (mean number ± standard deviation) | Percent Healing Rate |
| Control | — | 20 | 12.5 ± 6.0 ($mm^2$) | — |
| 1-(3'-dimethyl-aminopropoxy)-2,4-bis(3''-methylbenz-amido)-benzene | 10 | 20 | 6.9 ± 5.6*** | 45 |
| | 40 | 18 | 7.2 ± 5.1*** | 42 |

***$P<0.001$

The mean number and standard deviation for the control were 12.5 ± 6.0$mm^2$. While, for the test groups administered with 1-(3'-dimethylaminopropoxy)-2,4-bis(3''-methylbenzamido)-benzene in a dose of 10 mg/kg and 40 mg/kg, the values were 6.9 ± 5.6 ($mm^2$)and 7.2 ± 5.1 ($mm^2$) respectively, and were on a statistically significant lower level in comparison with those of the control.

EXAMPLE 4

1. Acute toxicity

Acute toxicity of 1-(3'-dimethylaminopropoxy)-2,4-bis(2''-methylbenzamido)-benzene, 1-(3'-dimethylaminopropoxy)-2,4-bis(3'-methylbenzamido)-benzene, 1-(n-B-dimethylaminopropyl)-carbamoyl)-2,4-bis(2''-methylbenzamido)-benzene and 1-[N-(3-dimethylaminopropyl)-carbamoyl)-2,4-bis(3''-methylbenzamido)- benzene were observed by the use of ddY strain male mice (5 weeks old) which were administered orally or intravenously with one of the compounds.

In the case of intravenous administration, the hydrochloride of test compound was dissolved in a physiological saline solution and administered by injecting into a vein of the tail. $LD_{50}$ was determined by the "Up and Down" method.

When the administration was effected orally, the test compound was suspended in a 1% gum arabic aqueous solution and the suspension was administered orally by gavage. $LD_{50}$ was determined by the Litchfield and Wilcoxon method or Miller and Tainter method based on death rate of each group of rats 10 days after the administration of the compound.

Table IV

| | Acute toxicity in mice | |
|---|---|---|
| Test compound | Administration Route | $LD_{50}$ (mg/kg) |
| 1-(3'-dimethylaminopropoxy)-2,4-bis(2''-methylbenzamido)-benzene | i.v.* | 42 a) |
| | oral | 2520 b) |
| 1-(3'-dimethylaminopropoxy)-2,4-bis(3''-methylbenzamido)-benzene | i.v. | 38 a) |
| | oral | 4700 b) |
| 1-[N-(3'-dimethylaminopropyl)-carbamoyl]-2,4-bis(2''-methylbenzamido)-benzene | i.v. | 111 a) |
| | oral | >11000 |
| 1-[N-(3'-dimethylaminopropyl)-carbamoyl]-2,4-bis(3''-methylbenzamido)-benzene | i.v. | 88 a) |
| | oral | 5100 c) |

Figure 2:
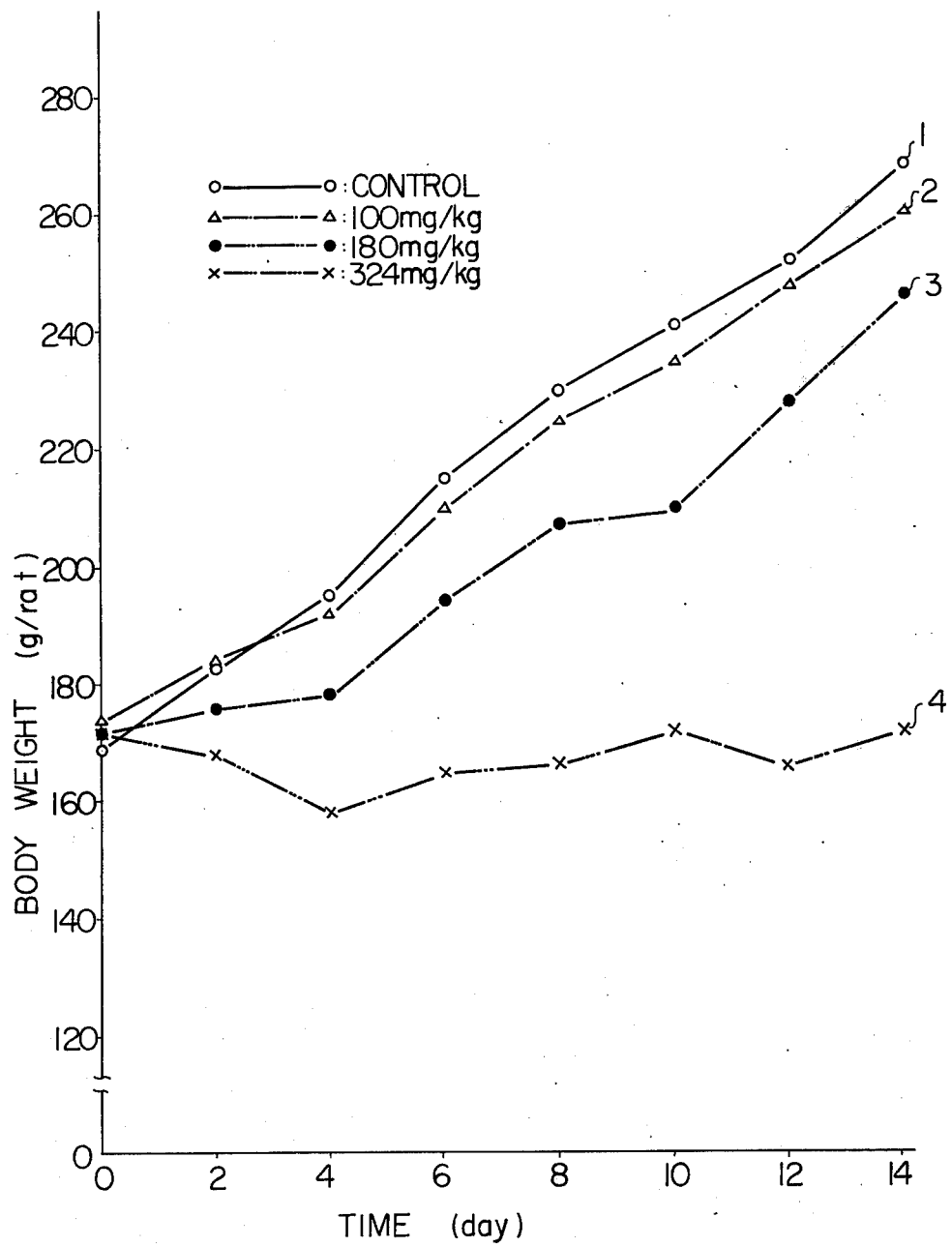
Figure 3:
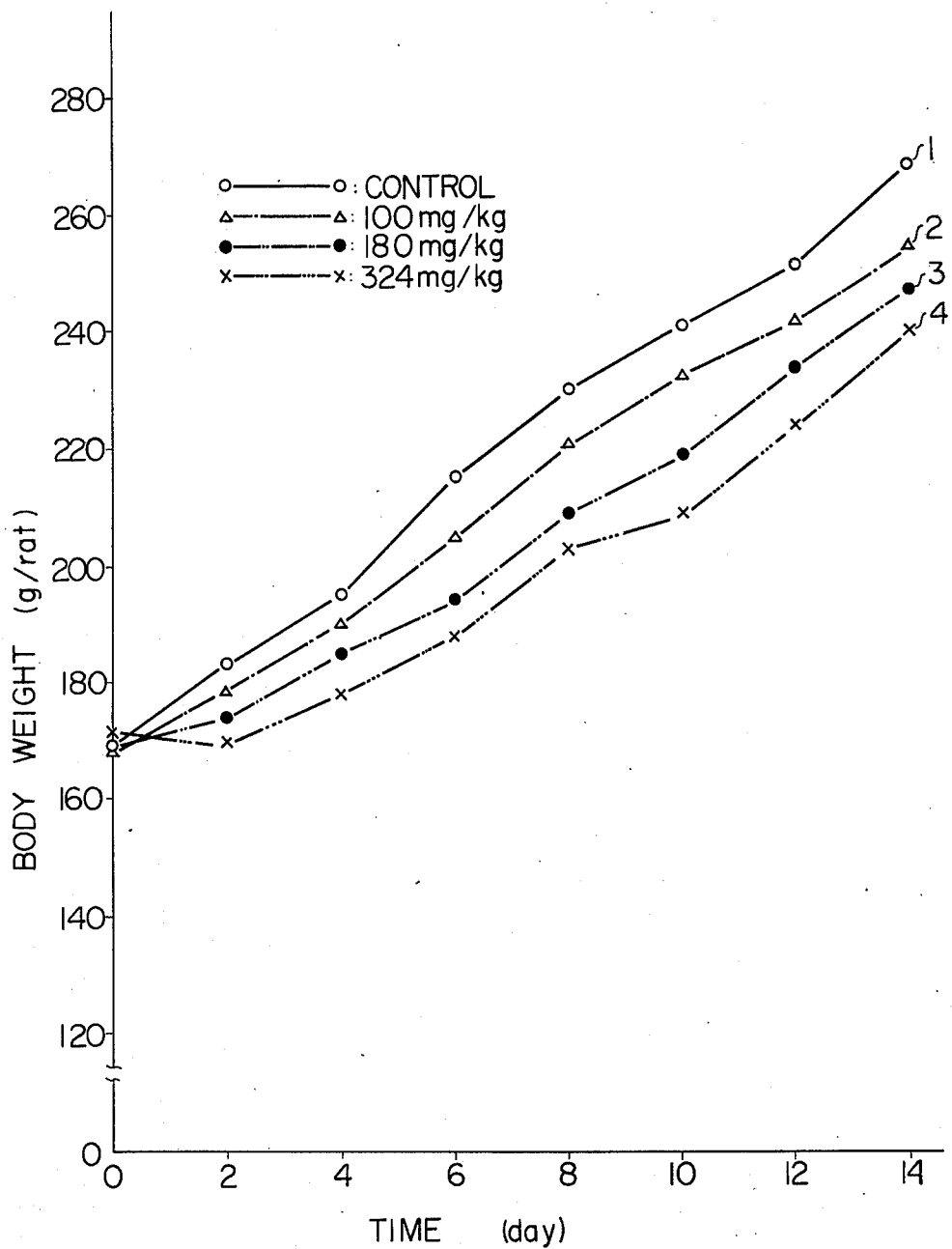
Figure 4:
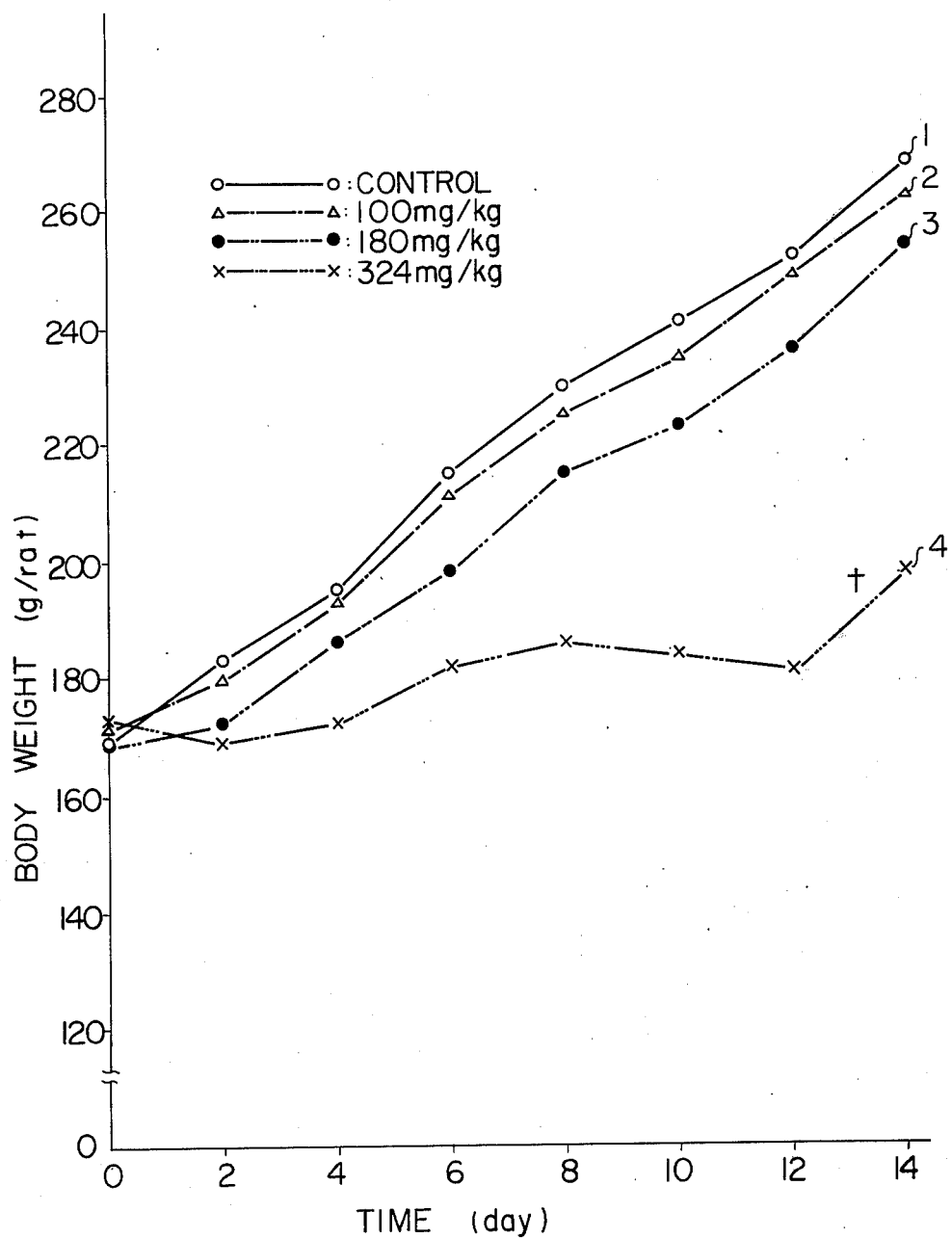

*intravanous
a) Up and Down Method
b) Litchfield and Wilcoxon Method
c) Miller and Tainter Method (2). Toxicity by repeated administration for two weeks Wistar strain male rats (6 weeks old) were divided into 13 groups of 5 members each, and each group was orally administered with 1-(3'-dimethylaminopropoxy)-2,4-bis(2''-methylbenzamido)-benzene, 1-(3'-dimethylaminoproxyl)-2,4-bis(3''-methylbenzamido)-benzene, 1-[N-(3'-dimethylamino-propyl)carbamoyl]-2,4-bis(2''-methylbenzamido)-benzene and 1-[N-(3'-dimethylaminopropyl)-carbamoyl]-2,4-bis(3''-methylbenzamido)-benzene, in a predetermined dose once a day for 14 days. The increase in body weight thereof was measured while the administration continued. Change of body weight of the rats was graphed separately as FIGS. 1, 2, 3 and 4 on the basis of individual test compound administered. Each group receiving a test compound in a dose of 100 mg/kg exhibited normal increase in body weight relative to the control group but, some inhibition of increase in body weight was observed at a dose level of 180 mg/kg. In contrast, in a dose of 324 mg/kg, the reduction in body weight was observed in the group receiving 1-(3'-dimethylaminopropoxy)-2,4-bis(2''-methylbenzamido)-benzene and three rats died by the twelveth day or after the start of the administration; remarkable inhibition of increase in body weight was observed in the groups receiving 1-(3'-dimethylaminopropoxy)-2,4-bis(3''-methylbenzamido)-benzene or 1-[N-(3''-dimethylaminopropyl)-carbamoyl]-2,4-bis(3''-methylbenzamido)-benzene; and some inhibition of increase in body weight was observed in the group receiving 1-[N-(3'-dimethylaminopropyl)-carbamoyl]-2,4-bis(2''-methylbenzamido)-benzene.

EXAMPLE 5 a. Capsules

Pulverized 1-(3'-dimethylaminoproxy)-2,4-bis(3''-methylbenzamido)-benzene (40 g), lactose (418 g) and magnesium stearate (2 g) were thoroughly mixed and hard gelatin capsules each weighing 65 mg were filled with 230 mg each of the mixture.

b. Pulverized 1-[N-(3'-dimethylaminopropyl)-carbamoyl]-2,4-bis (3''-methylbenzamido)-benzene (50 g) lactose (404 g) crystalline cellulose (45 g) and magnesium stearate (1 g) were thoroughly mixed to form powder.

c. Tablet 1

Pulverized 1-(3'-dimethylaminopropoxy)-2,4-bis (3'-methylbenzamido)-benzene (60) lactose (250 g) crystalline cellulose (72 g) corn starch (14 g) and magnesium stearate (4 g) were thoroughly mixed and, with a tablet machine the mixture was formed into tablets, each tablet being 8 mm in diameter and 200 mg in weight.

d. Tablet - 2

After being passed through a screen of 50 mesh, 1-[N-(3'-dimethylaminopropyl]-carbamoyl]-2,4-bis(2''-methylbenzamido)-benzene (100 g), lactose (273 g) and calcium carboxymethyl cellulose (20 g) were mixed, and then the mixture was kneaded with a corn starch paste made of corn starch (4g) and water. The resulting mixture was granulated by a granulating machine and dried. The granules were passed through a screen of 14 mesh. After addition of and mixing with magnesium stearate (3 g), the mixture was formed into tablets, each being 8 mm in diameter and 200 mg in weight.

e. Parenteral Injections

Pulverized 1-(3'-dimethylaminopropoxy)-2,4-bis(2''-methylbenzamido)-benzene (5 g) was mixed with benzyl alcohol (7 ml) followed by adding 1N-hydrochloric acid (11.5 ml) and distilled water (50 ml) and the mixture was heated at a temperature of from 50° to 60° C to completely dissolve the active compound in water. After cooling the solution to room temperature, distilled water was added to the solution to bring the total volume to 1 l. The resulting solution was filtered through a 0.45 μ membrane filter and the filtrate was charged in brown ampules each 2 ml in volume. Just after substitution of nitrogen gas for the space in ampules, they were melt-sealed and sterilized in an autoclave at 121° C for 20 minutes.

What is claimed is:

1. A pharmaceutical composition for prevention and treatment of peptic ulcer and gastritis of a mammal including human being comprising a bis(benzamido)-benzene derivative represented by the formula

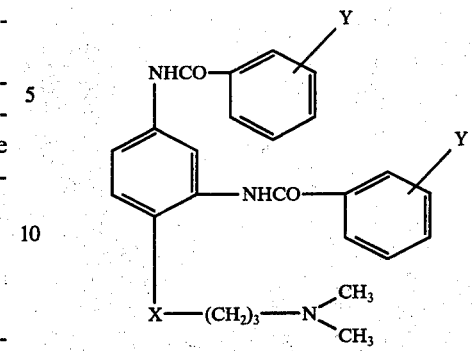

wherein X is oxygen and Y is methyl attached to o- or m-position of benzene nucleus or an acid addition salt thereof in an amount sufficient to prevent and treat the gastritis and peptic ulcer and a pharmaceutically acceptable carrier.

2. A pharmaceutical composition according to claim 1, wherein a mammal the peptic ulcer and gastritis of which are to be prevented and treated is a human being.

3. A pharmaceutical composition according to claim 1, wherein a mammal the peptic ulcer and gastritis of which are to be prevented and treated in monkey, bovine, horse, dog, cat or pig.

4. A pharmaceutical composition according to claim 1, wherein the form of said composition is suitable for oral administration.

5. A pharmaceutical composition according to claim 4 wherein said form of the composition in suspension, solution, tablet, granule, powder or capsule.

6. A pharmaceutical composition according to claim 4 wherein the amount of the bis(benzamido)-benzene derivative in said composition is present in an amount sufficient to realize the administration in an amount of from 0.01 to 100 mg/kg.body weight per day in terms of an active ingredient.

7. A pharmaceutical composition according to claim 4 wherein the bis(benzamido)-benzene derivative in said composition is present in an amount sufficient to realize the administration in an amount of from 0.05 to 20 mg/kg. body weight per day in terms of an active ingredient.

8. A pharmaceutical composition according to claim 1 wherein the form of said composition is suitable for injection.

9. A pharmaceutical composition according to claim 8 wherein the bis(benzamido)-benzene derivative in said composition is present in an amount sufficient to realize the administration in an amount of from 0.002 to 10 mg/kg. body weight per day in terms of an active ingredient.

10. A pharmaceutical composition according to claim 8 wherein the bis(benzamido)-benzene derivative in said composition is present in an amount sufficient to realize the administration in an amount of from 0.01 to 2 mg/kg. body weight per day in terms of an active ingredient.

11. A method for the prevention and treatment of peptic ulcer and gastritis of a mammal including human being which comprises administering to a mammal a pharmaceutical composition comprising an effective therapeutic amount for said purpose of a bis(benzamido) benzene derivative represented by the formula

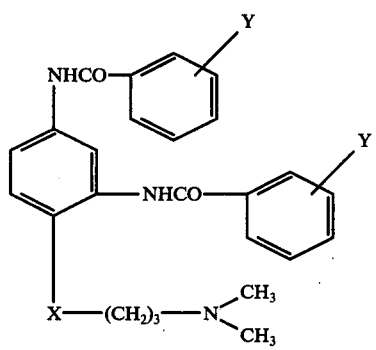

wherein X is oxygen and Y is methyl attached to a carbon atom at o- or m-position of benzene nucleus or an acid addition salt thereof, and a pharmaceutically acceptable carrier.

12. A method according to claim 11 wherein said composition is orally administered to a mammal in an amount of from 0.01 to 100 mg/kg.body weight per day in terms of an active ingredient.

13. A method according to claim 12 wherein said amount is of from 0.05 to 20 mg/kg.body weight in terms of an active ingredient.

14. A method according to claim 11 wherein said composition was administered by injection to a mammal in an amount of from 0.002 to 10 mg/kg.body weight per day in terms of an active ingredient.

15. A method according to claim 14 wherein said amount is of from 0.01 to 2 mg/kg body weight per day in terms of an active ingredient.

16. A method according to claim 11 wherein said mammal the peptic ulcer and gastritis of which are to be prevented and treated is human being.

17. A method according to claim 11 wherein said mammal the peptic ulcer and gastritis of which are to be prevented and treated is monkey, bovine, horse, dog, cat or pig.

* * * * *

UNITED STATES PATENT AND TRADEMARK OFFICE
CERTIFICATE OF CORRECTION

PATENT NO. : 4,038,416
DATED : July 26, 1977
INVENTOR(S) : MORI et al

It is certified that error appears in the above-identified patent and that said Letters Patent are hereby corrected as shown below:

Column 1, line 46, delete "wereadministered" and insert
--were administered--

Column 1, line 47, delete "were administered--

Column 1, lines 52-54, delete "1-[N-(3'-dimethylaminopropyl)-carbamoyl] 2,4-bis(3"-methylbenzamido)-benzene" and insert --1-[N-(3'-dimethylaminopropyl)-carbamoyl]-2,4-bis(3"-methylbenzamido)-benzene--

Column 2, lines 24-25, delete "1-3'-dimethylaminopropoxy)-2,4-bis(3"-methylbenzamido)-benzene" and insert --1-(3'dimethylaminopropoxy)-2,4-bis(3"-methylbenzamido)-benzene--

Column 4, lines 37-38, delete "1-(3'-dimethylaminopropoxy)-2,4-bis)3"-methylbenzamido-benzene" and insert --1-(3'-dimethylaminopropoxy)-2,4-bis(3"-methylbenzamido)-benzene--

Column 7, lines 4-6, delete "1-[N-(3'-dimethylaminopropyl)-carbamoyl[-2,4-bis(3"-methylbenzamido)-benzene" and insert --1-[N-(3'-dimethylaminopropyl)-carbamoyl]-2,4-bis(3"-methylbenzamido)-benzene--

Column 7, lines 67-68 through
Column 8, line 1, delete "1-(3'-dimethylaminopropoxy)-2,4-bis(3'-methylbenzamido)-benzene and insert --1-(3'-dimethylaminopropoxy)-2,4-bis(3"-methylbenzamido)-benzene

UNITED STATES PATENT AND TRADEMARK OFFICE
CERTIFICATE OF CORRECTION

PATENT NO. : 4,038,416
DATED : July 26, 1977
INVENTOR(S) : MORI et al

It is certified that error appears in the above-identified patent and that said Letters Patent are hereby corrected as shown below:

Column 8, lines 1-2, delete "1-(n-B-dimethylaminopropyl)-carbamoyl)-2,4-bis(2"-methylbenzamido)-benzene" and insert --1-[N-(3'-dimethylaminopropyl)-carbamoyl]-2,4-bis(2"-methylbenzamido)-benzene--

Column 8, lines 2-4, delete "1-[N-(3-dimethylaminopropyl)-carbamoyl)-2,4-bis(3"-methylbenzamido)-benzene" and insert --1-[N-(3'-dimethylaminopropyl)-carbamoyl]-2,4-bis(3"-methylbenzamido)-benzene--

Column 9, lines 4-5, delete "1-[N-(3"-dimethylaminopropyl)-carbamoyl]-2,4-bis(3"-methylbenzamido)-benzene" and insert --1-[N-(3'-dimethylaminopropyl)-carbamoyl]-2,4-bis(3"-methylbenzamido)-benzene--

Column 9, lines 26-27, delete "1-(3'-dimethylaminopropoxy)-2,4-bis (3'-methylbenzamido)-benzene" and insert --1-(3'-dimethylaminopropoxy)-2,4-bis(3"-methylbenzamido)-benzene--

Column 9, line 27, delete "(60)" and insert --(60 g)--

Column 10, line 26, delete "in" and insert --is--

Column 10, line 32, delete "in" and insert --is--

UNITED STATES PATENT AND TRADEMARK OFFICE
CERTIFICATE OF CORRECTION

PATENT NO. : 4,038,416
DATED : July 26, 1977
INVENTOR(S) : MORI et al

It is certified that error appears in the above-identified patent and that said Letters Patent are hereby corrected as shown below:

Table IV, footnote, delete "intravanous" and insert
--intravenous--

Signed and Sealed this

Sixteenth Day of May 1978

[SEAL]

Attest:

RUTH C. MASON
*Attesting Officer*

LUTRELLE F. PARKER
*Acting Commissioner of Patents and Trademarks*